US007180042B2

United States Patent
Ito (10) Patent No.: US 7,180,042 B2
(45) Date of Patent: Feb. 20, 2007

(54) RADIOGRAPHIC IMAGE INPUT APPARATUS WHICH OBTAINS IMAGE CORRECTION VALUES BASED ON A SIZE OR VERSION OF A RADIOGRAPHIC RECORDING MEMBER

(75) Inventor: Tsuyoshi Ito, Hachioji (JP)

(73) Assignee: Konica Minolta Holdings, Inc., Tokyo (JP)

( * ) Notice: Subject to any disclaimer, the term of this patent is extended or adjusted under 35 U.S.C. 154(b) by 0 days.

(21) Appl. No.: 10/524,088
(22) PCT Filed: Aug. 14, 2003
(86) PCT No.: PCT/JP03/10302

§ 371 (c)(1),
(2), (4) Date: Feb. 9, 2005

(87) PCT Pub. No.: WO2004/016175

PCT Pub. Date: Feb. 26, 2004

(65) Prior Publication Data

US 2006/0000991 A1    Jan. 5, 2006

(30) Foreign Application Priority Data

Aug. 14, 2002  (JP) ............................ 2002-236489

(51) Int. Cl.
*H01L 27/00* (2006.01)
*G01N 23/04* (2006.01)
*H05G 1/64* (2006.01)

(52) U.S. Cl. ................... 250/208.1; 250/584; 250/587; 378/62; 378/98.8

(58) Field of Classification Search ............. 250/208.1, 250/214 VT, 214 R, 580–590; 382/132; 378/62, 98.8; 235/375, 376
See application file for complete search history.

(56) References Cited

U.S. PATENT DOCUMENTS

| 4,498,006 | A | * | 2/1985 | Horikawa et al. ........... 250/584 |
| 5,086,228 | A | * | 2/1992 | Kojima ....................... 250/587 |
| 5,331,441 | A | * | 7/1994 | Akuzawa et al. ............. 358/530 |
| 5,376,806 | A | * | 12/1994 | Hejazi ......................... 250/584 |
| 5,485,500 | A | * | 1/1996 | Baba et al. ................. 378/98.2 |
| 5,604,781 | A | * | 2/1997 | Suzuki et al. ................. 378/62 |
| 5,760,416 | A | * | 6/1998 | Tsuchiya .................... 250/584 |

FOREIGN PATENT DOCUMENTS

| JP | 64-86758 A | 3/1989 |
| JP | 9-19424 A | 1/1997 |
| JP | 9-113836 A | 5/1997 |
| JP | 9-191401 A | 7/1997 |
| JP | 2000-321690 A | 11/2000 |
| JP | 2000-350032 A | 12/2000 |
| JP | 2002-157587 A | 5/2002 |

* cited by examiner

*Primary Examiner*—Georgia Epps
*Assistant Examiner*—Pascal M. Bui-Pho
(74) *Attorney, Agent, or Firm*—Frishauf, Holtz, Goodman & Chick, P.C.

(57) ABSTRACT

An image input apparatus which includes a detection section (10) to detect radiographic image from a recording member (4) having radiographic image information recorded thereon, and reads the detected radiographic image, the image input apparatus including: a creation section (17) to create a plurality of correction values for correction of unevenness on the image or radiography sensitivity, in which the plurality of correction values correspond to a plurality of detection regions; a storage section (17) to store the created plurality of correction values; and a selecting section (13) to select an optimal correction value upon image reading, wherein the optimal correction value is used for the image reading.

8 Claims, 6 Drawing Sheets

UNEVENNESS CORRECTION DATA STRUCTURE
(RELATIONSHIP AMONG PLATE TYPE, SAMPLING PITCH AND PV)

| PLATE TYPE | SAMPLING PITCH | PLATE VERSION [PV] | |
|---|---|---|---|
| REGULAR | 200 μm | 000 to 299 | REGULAR 200 μm |
| | | 300 to 499 | RESERVE |
| | | 500 | REFERENCE AT TIME OF PRODUCTION OF REGULAR 200 μm |
| | 100 μm | 000 to 299 | REGULAR 100 μm |
| | | 300 to 499 | RESERVE |
| | | 500 | REFERENCE AT TIME OF PRODUCTION OF REGULAR 100 μm |
| MAMMOGRAPHY PLATE | 50 μm | 501 to 799 | MAMMOGRAPHY PLATE 50 μm |
| | | 800 to 899 | RESERVE |
| | | 900 | REFERENCE AT TIME OF PRODUCTION OF MAMMOGRAPHY PLATE |

FIG.3

SENSITIVITY CORRECTION DATA STRUCTURE

| PLATE TYPE | PLATE VERSION [PV] | |
|---|---|---|
| REGULAR | 000 to 299 | REGULAR 200μm |
| | 300 to 499 | RESERVE 200μm |
| | 500 | REFERENCE AT TIME OF PRODUCTION OF REGULAR 200μm |
| | 000 to 299 | REGULAR 100μm |
| | 300 to 499 | RESERVE 100μm |
| | 500 | REFERENCE AT TIME OF PRODUCTION OF REGULAR 100μm |
| MAMMOGRAPHY PLATE | 501 to 799 | MAMMOGRAPHY PLATE 50μm |
| | 800 to 899 | RESERVE 50μm |
| | 900 | REFERENCE AT TIME OF PRODUCTION OF MAMMOGRAPHY PLATE 50μm |

FIG.4

STRUCTURAL IMAGE OF CORRECTION VALUE TABLE

| CASSETTE TYPE | PV | PITCH | PRESENCE/ABSENCE OF CORRECTION | CASSETTE SIZE | UNEVENNESS CORRECTION DATA | SENSITIVITY CORRECTION DATA |
|---|---|---|---|---|---|---|
| REGULAR | 500 | 200 | 1 | 14 × 17 inch SIZE | | HIGH, STANDARD, LOW SENSITIVITY |
| REGULAR | 500 | 100 | 1 | 14 × 17 inch SIZE | | |
| MAMMOGRAPHY CASSETTE | 900 | 50 | 1 | LARGE SIZE | | |
| REGULAR | 001 | 200 | 1 | 14 × 17 inch SIZE | | |
| REGULAR | 001 | 100 | 1 | 14 × 17 inch SIZE | | |
| REGULAR | 003 | 100 | 1 | 14 × 14 inch SIZE | | |
| MAMMOGRAPHY CASSETTE | 000 | 50 | 1 | SMALL SIZE | | |
| REGULAR | 006 | 100 | 1 | 14 × 17 inch SIZE | | |
| REGULAR | 300 | 100 | 1 | 14 × 17 inch SIZE | | |
| REGULAR | 300 | 100 | 1 | 14 × 17 inch SIZE | | |
| REGULAR | 008 | 100 | 1 | 14 × 11 inch SIZE | | |
| | | | 0 | | | |
| | | | 0 | | | |
| | | | 0 | | | |
| | | | 1 | | | |
| COMMON INFORMATION FOR UNEVENNESS AND SENSITIVITY (HEADER INFORMATION) | | | | UNEVENNESS CORRECTION INFORMATION | | SENSITIVITY CORRECTION INFORMATION |

RADIOGRAPHIC IMAGE INPUT APPARATUS WHICH OBTAINS IMAGE CORRECTION VALUES BASED ON A SIZE OR VERSION OF A RADIOGRAPHIC RECORDING MEMBER

This application is a U.S. National Phase Application under 35 USC 371 of International Application PCT/JP2003/010302 filed Aug. 14, 2003.

TECHNICAL FIELD

The present invention relates to an image input apparatus and an image input method for inputting radiographic image information, which are mainly used in the medical field.

BACKGROUND ART

There has been publicly known an image input apparatus which irradiates a subject with radiation emitted from a radiation generating device for a sickness diagnosis etc., reads the radiographic image formed through the radiation having penetrated the subject, and inputs the image information. Such an image input apparatus includes: a system which condenses photo-stimulated light generated by scanning with a laser beam a photostimulable phosphor plate having the radiographic image information accumulated therein, and performs photoelectric conversion with a photomultiplier (hereinafter may be referred to as PMT) to convert the light into an electric signal (CR type); and a system which has a function to convert X-ray energy irradiated through the subject into an electric signal for re-structuring the X-ray energy as an X-ray penetration image, and configured of a flat-plate-shaped X-ray image flat detection device (X-ray flat panel detector) having a flat face of an area that sufficiently covers a human body part necessary for an image diagnosis (FPD type).

For example, in a CR type image input apparatus, unevenness in laser beam scanning with an optical system and unevenness in radiography sensitivities are generated due to the PMT that performs photoelectric conversion, and therefore, the unevennesses need to be corrected. Conventionally, such correction is performed using correction values created at the time of production of an image input apparatus. In general, correction value creation (calibration) in view of compensating of unevenness due to optical system is performed in accordance with a large cassette size or the like, and, by using the correction value obtained based on the large size, correction is performed over the large size to a smaller size. A plurality of correction values mentioned above may be created, for example, for each of sampling pitch differences, which are one of correction coefficients. However, the other correction coefficients (size, etc.) are collected into one, and therefore, even when reading is performed for a small size at the user's end, calibration has to be performed for the largest size upon creating correction values.

DISCLOSURE OF THE INVENTION

The present invention has been made in view of the above problem, and an object thereof is to provide an image input apparatus and an image input method capable of creating correction values for various sizes (detection regions) for easier operation, and, even when there are various plates (recording members), performing correction suitable therefor.

To attain the above object, according to one aspect of the invention, an image input apparatus of the present invention includes a detection section to detect radiographic image from a recording member having radiographic image information recorded thereon, and reads the detected radiographic image, the image input apparatus comprising: a creation section to create a plurality of correction values for correction of unevenness on the image or radiography sensitivity, in which the plurality of correction values correspond to a plurality of detection regions; a storage section to store the created plurality of correction values; and a selecting section to select an optimal correction value upon image reading, wherein the optimal correction value is used for the image reading.

For example, unlike the earlier development where a plate (recording member) of a large detection region has to be provided even when only a plate of a smaller detection region is used due to that a correction value for the large detection region needs to be created, with the image input apparatus of the present invention, it is only necessary to create only a correction value corresponding to the smaller detection region. Thus, operation thereof becomes easy.

In this specification, "to select an optimal correction value" means to select a correction value of a case where the detection regions of the recording members used upon image reading (creation) and upon correction are the same or larger, a correction value of a case where the recording member having a correction value for unevenness on an image or for radiography sensitivity is created therein and the recording member used upon image reading are the same, and a correction value having close information concerning such as creation date or time and the composition thereof, when the same recording member does not exist.

Preferably, the plurality of correction values are created for each of a plurality of correction coefficients, and stored in the storage section. Moreover, preferably, concerning the correction of unevenness on the image, among the correction values created to correspond to the plurality of detection regions, a relevant correction value is used for correction of an image of a detection region not larger than a predetermined region. Further, preferably, the apparatus further has a function to un-select a correction value of a region not larger than the predetermined region, and search for a different correction value, among the created correction values, when an image of a detection region not smaller than the predetermined region is inputted upon the image reading.

The apparatus may further comprise another storage section to separately store an unconditionally-used correction value used when the optimal correction value does not exist. Moreover, in the correction of unevenness on the image, when an image having a region not smaller than the detection regions required to create the plurality of correction values is detected, the same correction value as a correction value on left-right/upper-lower boundaries is expanded (extended) in left-right/upper-lower directions outside the detection region. Thus, generation of difference in concentrations caused due to absence of a correction value of portions outside the region is reduced, and correction can be performed without a sudden concentration change. Note that, since the expanded correction value is a presumed or supposed correction value, the correction value is sometimes unused. In this case, it is preferable that correction is performed using a function having the correction value capable of unconditional correction.

Further, a correction value of a region to be used may be created beforehand and stored in the storage section, and correction may be performed by using the correction value, on images having a plurality of regions.

In the image input apparatus, it is preferable that the storage section records image information, stores a plurality of version data containing information about the recording member from which the image recorded thereon is detected by the detection section, and stores each of the correction values corresponding to the version data, and the selecting section selects the optimal correction value based on relevant version data. When the relevant version data does not exist, a correction value selected based on adjacent version data may be used for the image reading, or a correction value selected based on adjacent obsolete version data may be used for the image reading.

For example, when a plate is used as the recording member in the CR type, the version data may be the version number of the plate, and, when a detector is used as the recording member in the FPD type, the version data may be the version number of the detector. Thus, by using the version data as a key, it is possible to study the properties (such as creation condition) of the correction value, and, when the correction value is suitable, the correction value is used, and, when the correction value is not suitable, a suitable correction value among adjacent correction values can be searched for.

Preferably, the apparatus further comprises another storage section to separately store an unconditionally-used correction value used when the correction values do not exist or a correction value corresponding to the relevant version data does not exist adjacently, wherein, when the relevant version data does not exist, the unconditionally-used correction value is used for the image reading.

The apparatus may further have a function to warn that the unconditionally-used correction value is used, when the relevant correction value does not exist and the unconditionally-used correction value is used. More concretely, examples of the warning function include such as beeping an alarm sound or performing alarming display when the unconditionally-used correction value is used.

The apparatus may further comprise an erasing section to first erase an obsolete correction value, when the storage section to store the plurality of correction values reaches the limit thereof or the number of correction values to be stored is limited. In this case, it is preferable that the erasing section does not erase the unconditionally-used correction value.

The apparatus may further have a function to perform selection according to a condition which is provided beforehand or provided upon the image reading through a network or by an information input device, to select the optimal correction value.

Preferably, as the optimal correction value, a part of or all of version data, a detection region (cassette size, etc.), an image sampling pitch, a time difference between reading speeds of each of main-scanning/sub-scanning, and data on an X-ray tube used. In this case, it is preferable that the apparatus stores, in the storage section, based on the version data as a key, the part of or the all of the region, image sampling pitch, time difference between reading speeds of each of main-scanning/sub-scanning, and data on an X-ray tube used, and uses the version data as a search key upon correction value selection.

Moreover, the apparatus may include an unevenness correction value corresponding to an image area, store a plurality of correction values for each of X-ray tubes to be used, and select a corresponding correction value therefrom when a relevant X-ray tube is used. In this case, the apparatus may receive information on a relevant X-ray tube through a network.

Thus, management for each correction value level becomes possible, and it is possible to select a correction value according to desired image precision, when there is a correction value corresponding to an image area to perform complete two-dimensional correction, a correction value of a pixel skipping level is required, and a correction value of a level for eliminating only unevenness caused due to the laser scanning direction of the optical system.

BEST MODE FOR CARRYING OUT THE INVENTION

Figure 1:
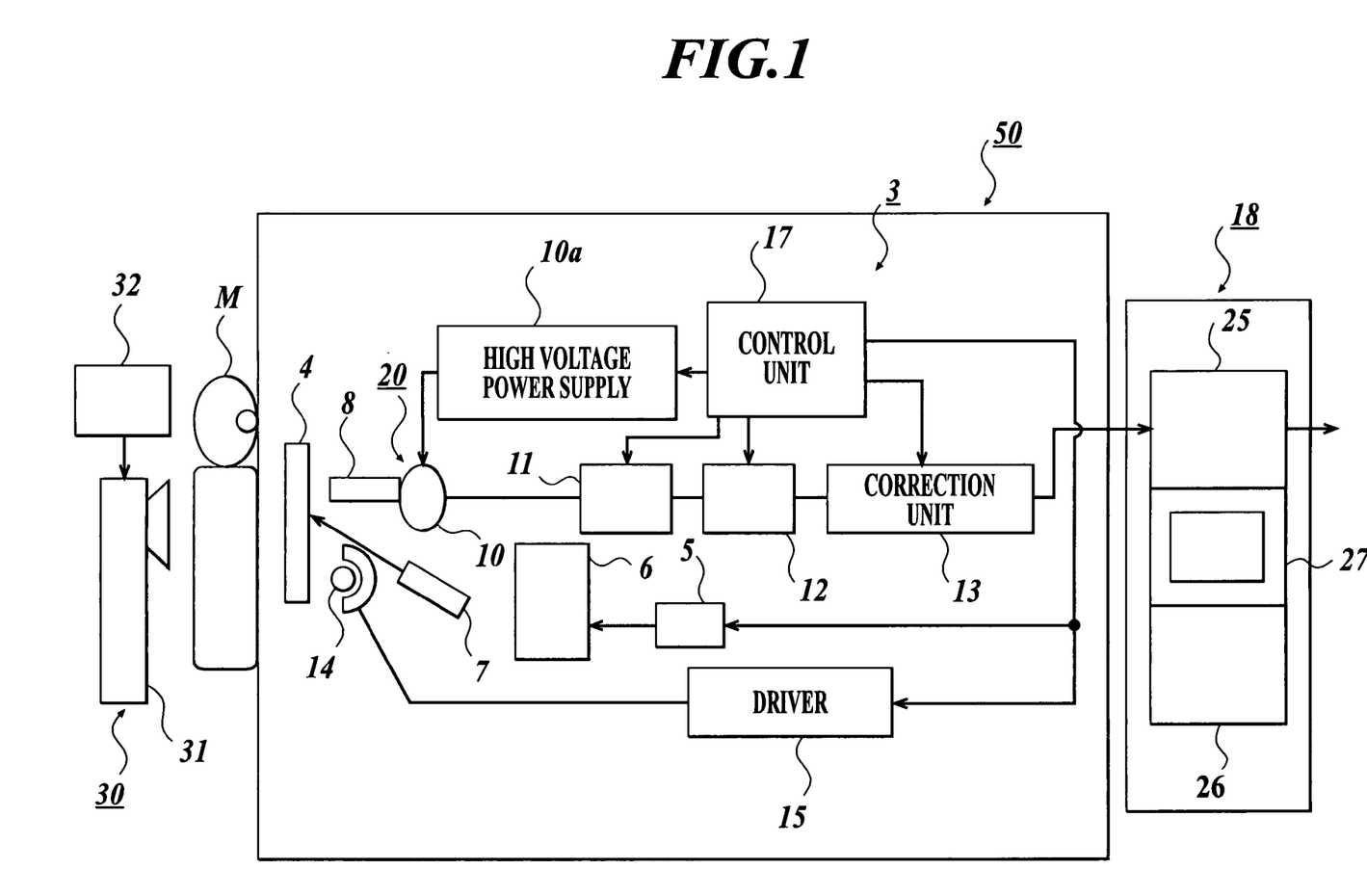
FIG. 1 is a schematic view showing a radiographic image input apparatus according to an embodiment of the present invention.

Hereinbelow, an embodiment of the present invention will be described. FIG. 1 is a schematic view of a radiographic image input apparatus according to an embodiment of the present invention. A radiographic image input apparatus 50 in FIG. 1 is a radiographic image input apparatus of CR type to input information on a radiographic image by reading radiographic image recorded on a photostimulable phosphor plate 4 as a recording medium, and the apparatus has a form as shown in FIG. 1.

An input device (image input device) 3 in FIG. 1 utilizes photostimulable phosphor, which stores part of radiation energy upon exposure of a radiographic image and shows photo-stimulated light in proportion to the accumulated radiation energy when irradiated with excitation light such as visible light or a laser beam subsequent to the exposure. Radiographic image information on a subject M such as a human body, which information is obtained by irradiating the subject M with radiation emitted from a radiation generating device 30, is temporarily stored and recorded on a sheet-shaped photostimulable phosphor plate (recording member) 4 prepared by laminating storage phosphor onto a supporting body. The photostimulable phosphor plate 4 is scanned with a laser beam to sequentially cause photostimulated luminescence, and the photo-stimulated light is sequentially read photoelectrically with a photoelectric reading unit 20 to obtain an image signal. Then, in the input device 3, the photostimulable phosphor plate 4 is irradiated with erasing light after the image signal is read, and the radiation energy remaining on the plate is released to be ready for the next radiography. The radiation generating device 30 includes a radiation emitting section 31 to emit radiation from a tube to the subject M, and a control section 32 to control the radiation emitting section 31.

The input device 3 includes: the photostimulable phosphor plate 4 on which radiographic image information on a subject is recorded; a laser light source unit 6 which includes a laser diode to generate a laser beam as excitation light emitted to the photostimulable phosphor plate 4, and the like; a laser drive circuit 5 to drive the laser light source unit 6; an optical system 7 to allow the photostimulable phosphor plate 4 to be scanned with the laser beam from the laser light source unit 6; and the photoelectric reading unit 20 which condenses photo-stimulated light excited by the excitation laser beam and performs photoelectric conversion to obtain an image signal.

The photoelectric reading unit 20 includes: a condenser body 8 to condenses photo-stimulated light excited by the excitation laser beam; a photomultiplier (PMT) 10 which performs photoelectric conversion on light condensed by the condenser body 8 and functions as a detection device (detection section); a high voltage power supply 10*a* to apply voltage to the photomultiplier 10; a current-voltage conversion unit 11 to perform logarithmic voltage conversion on a current signal transmitted from the photomultiplier 10; an A/D conversion unit 12 to perform A/D conversion on an analog signal transmitted from the current-voltage conversion unit 11; and a correction unit 13 to perform various corrections on the converted digital signal. The photoelectric reading unit 20 transfers the digital signal of the read radiographic image data to a controller 18. The correction unit 13 includes a memory to store correction data and the like, and is capable of correcting unevenness in concentrations caused by the optical system 7 or the condenser body 8, as one of the various corrections, by using the correction data. Moreover, the correction unit 13 is capable of checking the offset value for controlling the high voltage power source 10*a* to correct unevenness in sensitivities of the photomultiplier (PMT), thus the unevenness in sensitivities can be corrected.

The input device 3 further includes: a halogen lamp 14 which radiates erasing light to release radiation energy remaining on the photostimulable phosphor plate after image signal reading; and a driver 15 to drive the halogen lamp 14. Moreover, the input device 3 includes a control unit 17 to control each of the laser drive circuit 5, high voltage power supply 10*a*, current-voltage conversion unit 11, A/D conversion unit 12, correction unit 13, and driver 15. The laser light source unit 6, optical system 7, condenser body 8, photomultiplier 10, and halogen lamp 14 of the input device 3 are fixed to the input device 3, and the plate 4 is moved in the sub-scanning direction perpendicular to the laser scanning direction by a mechanism serving as a sub-scanning unit (not shown) to convey the plate 4. The sub-scanning unit performs sub-scanning to read the image by moving at the time of image reading. Further, the radiographic image information remaining on the photostimulable phosphor plate 4 is erased by light emitted from the halogen lamp while the sub-scanning unit is moving. Thus, the radiographic image recorded on the photostimulable phosphor plate 4 is automatically read and the information on the image is inputted. Moreover, the image remaining after the image reading is erased, to permit the next radiography.

The controller 18 includes a personal computer main body 25, a keyboard 26, a monitor display unit, and a touch panel monitor input unit 27. The controller 18 temporarily stores the digital signal of radiographic image data received from the input device 3, performs image processing, controls display and image processing on the monitor display unit 27 in accordance with an operational input from the keyboard 26, and outputs the radiographic image data on which the image processing has been performed.

Next, an operation of creating a correction value (calibration) will be explained. Data required for calibration (correction coefficient) includes cassette sizes (for example, 14×17 inch size, 14×14 inch size, 14×11 inch size, 10×12 inch size, 8×10 inch size, etc.), plate versions (PV), image sampling pitches, and plate types (regular plate, mammography plate, etc.).

Storage tables of correction values suitable for each plate version and sampling pitch are stored in the correction unit 13 on the input device 3 side. Here, a maximum of 10 tables (high and normal definitions for general radiography, and high definition for mammography: 30 tables in total) are stored. When the number of the tables exceeds ten, obsolete data (i.e., data of small numbered plate version) is overwritten. Note that overwrite protection is set to a piece of reference data at the time of production of the input device (unconditionally-used correction value), among data in each ten table.

Figure 2:
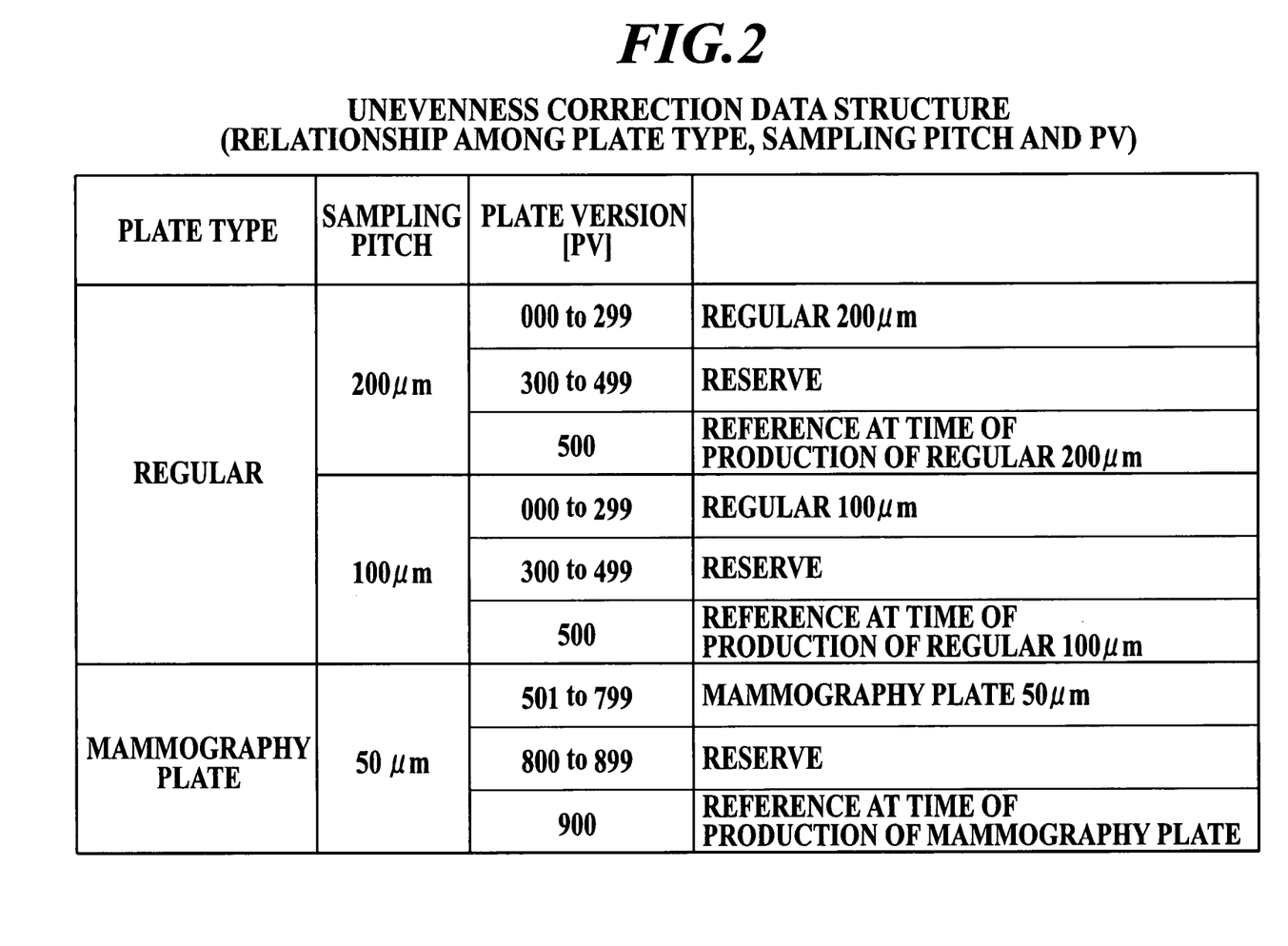
FIG. 2 is a view showing a storage structure of an unevenness correction value.
Figure 3:
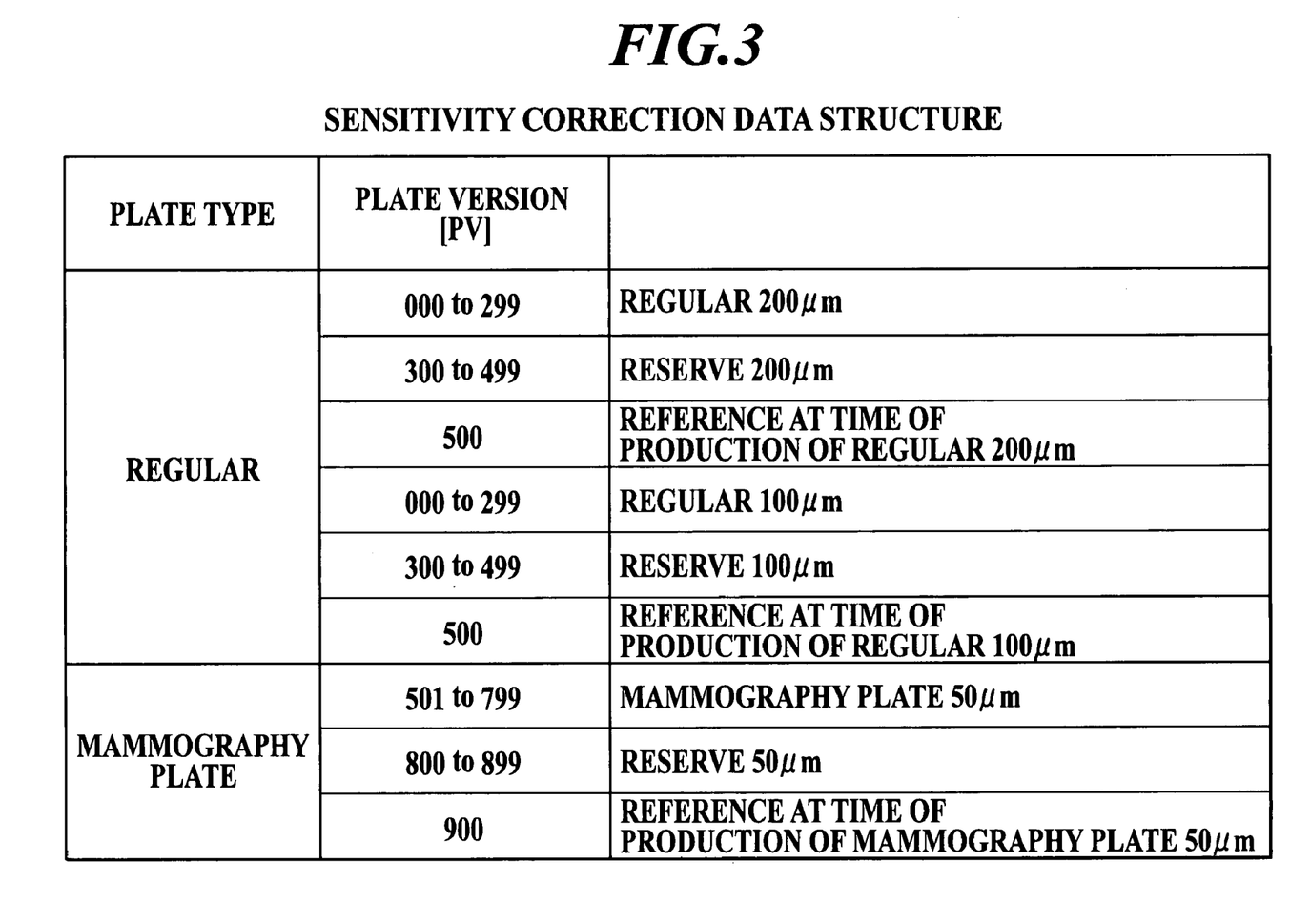
FIG. 3 is a view showing a storage structure of a sensitivity correction value.

An unevenness correction value table structure is shown in FIG. 2, and a sensitivity correction value table structure is shown in FIG. 3. Concerning a sensitivity correction value, there are three kinds of sensitivity correction data, for example, high sensitivity, standard sensitivity, and low sensitivity, in the plate versions shown in FIG. 3.

Here, a plate version is collective information on a plate, and is a number assigned to a plate in accordance with the production date or time of the plate, the composition thereof, etc. Plates having close production date or time, or similar composition, are grouped and classified into either of "000–299", "300–499" and "500" (see FIGS. 3 and 4).

Next, the difference between use of an unevenness correction value creating method (calibration) at the time of production and use of an additional correction value creating method at the user's end will be explained.

Among the correction values created at the time of production, at least one piece of data serves as an unconditionally-used correction value, and thus calibration is performed for the largest cassette size (here, for ordinary radiography, always 14×17 inch size). Any plate version is acceptable. Similarly, for mammography, the largest size is applied. At this time, the plate version exclusive for the time of production is assigned to the correction data.

As to calibration performed at the user's end, calibration is performed for the largest plate size of a cassette possibly used on site. A plate version is a value given to each plate. In sensitivity calibration, the plate versions are classified at the time of production and at the user's end on site, in the same way as that of the unevenness correction described above. Here, a plate version given to each plate is, for example, a numeric value assigned according to difference between plate production lots. The plate version may be printed in the form of barcode on the cassette surface, and information is extracted with a barcode reader.

A description will be given of a method of selecting a correction value upon image reading concerning sensitivity correction, and an operation method thereof.

Figure 4:
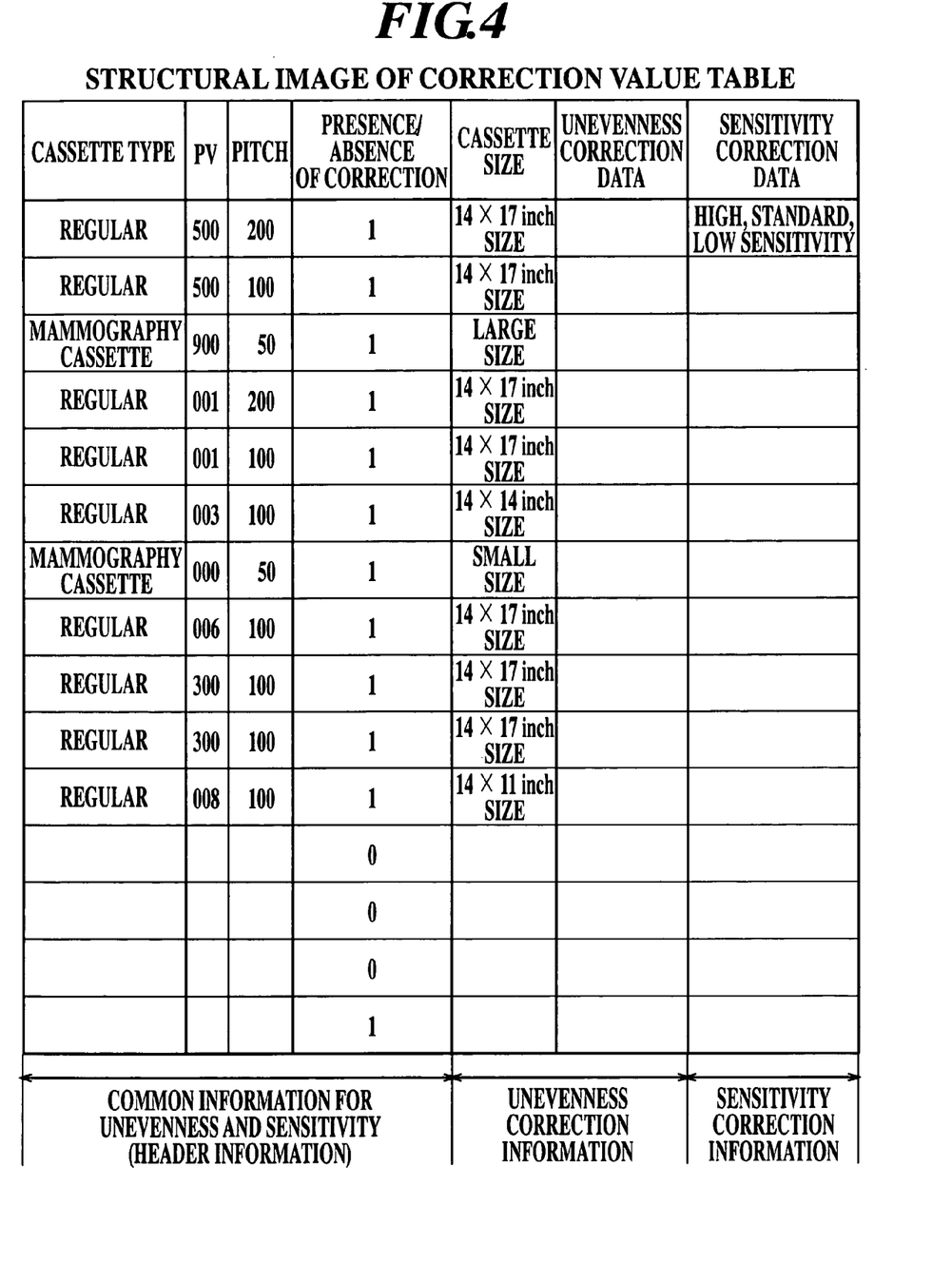
FIG. 4 is a view showing a structural image of a correction value table.

For example, when the same cassette type and sampling pitch are applied upon calibration and image reading, a correction value of a lower version (i.e., plate version of a smaller number) is searched for. When there is no correction value on the lower side, a correction value of a higher version (i.e., plate version of a larger number) is searched for. An example of a structure of data stored for the respective plate versions is shown in FIG. 3. An example of a table structure at the time of operation thereof is shown in FIG. 4. Here, when there is no relevant version on the lower and higher sides (i.e., when there is no plate version adjacently), the correction value created upon production of a plate version 500 (900 in the case of mammography) is used, in a case where the operation example in FIG. 4 is employed.

Figure 5:
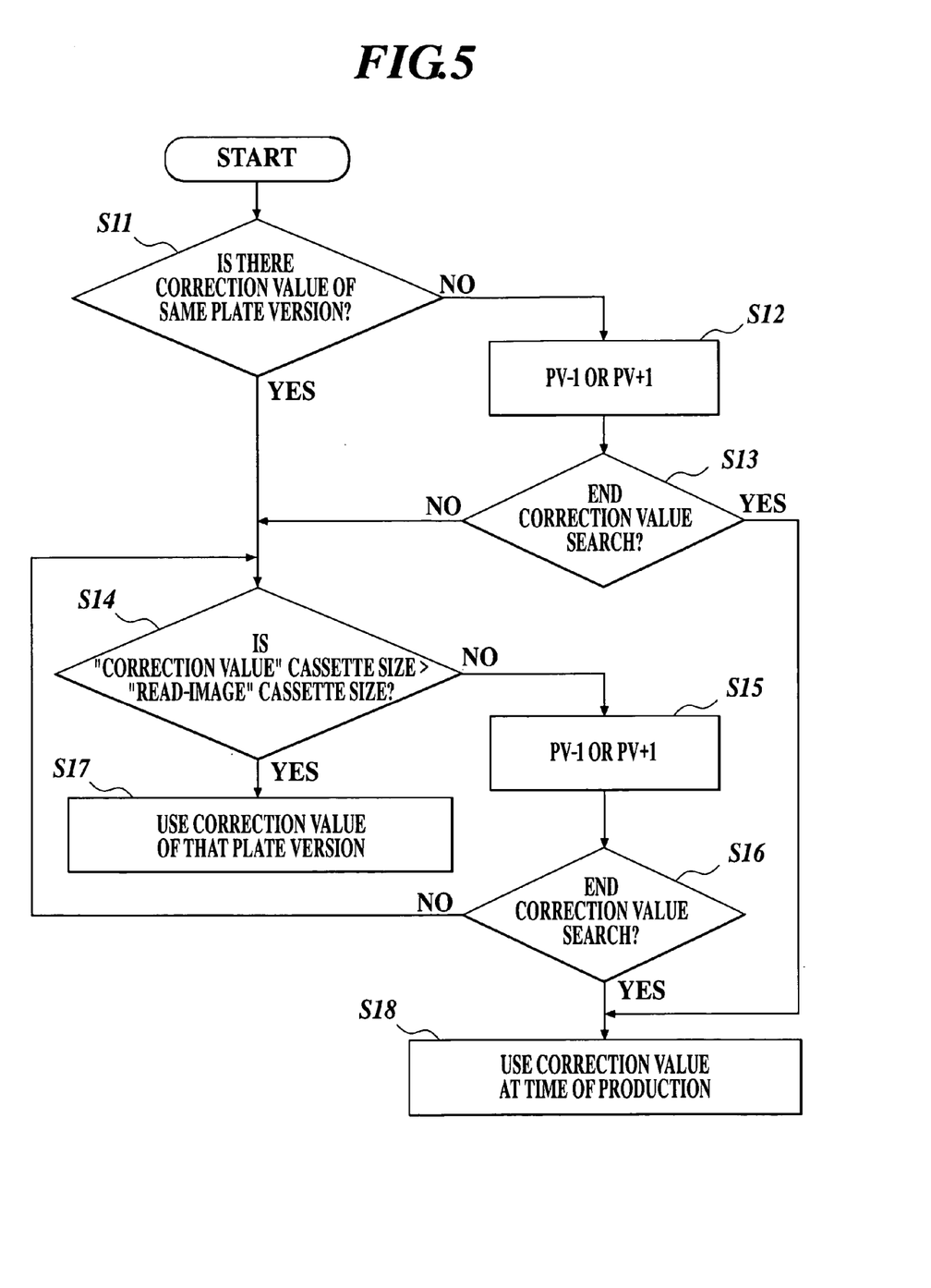
FIG. 5 is a flow chart showing an example of an unevenness amendment selection procedure.

Next, with reference to FIG. 5, a description will be given of a method of selecting a correction value upon image reading concerning unevenness correction, and an operation method thereof.

For example, when the same sampling pitch is applied upon calibration and image reading, the cassette size of the correction value (i.e., at the time of calibration) is larger, and a plate of non-applicable version is inserted (Step S11; No), a correction value of a lower version is searched for. When there is no correction value on the lower side, the higher side is searched. That is, an adjacent plate version is searched for (Step S12). When there is no adjacent plate version, correction value search is ended (Step S13; Yes), the correction value created upon production of the plate version 500 (900 in the case of mammography) is used (Step S18). An example of structure of data stored for the respective plate versions is shown in FIG. 2. A table structure at the time of operation thereof is shown in FIG. 4.

When the same sampling pitch and different cassette sizes are applied, and there is a correction value of the same plate version (Step S11; Yes) or there is no adjacent plate version in the above-mentioned Step S12 (Step S13; No), a correction value of a lower plate version is searched for when the relation "inserted cassette>cassette size at the time of calibration" is established (Step S14; No), and search is performed until the plate version for which a correction value satisfying "inserted cassette<cassette size at the time of calibration" is created is found. When the correction value satisfying "inserted cassette<cassette size at the time of calibration" is found, the correction value of the relevant plate version is used (Step S17). In contrast, when the correction value is not found on the lower side, the higher side is searched (Step S15). When the correction value is still not found, the correction value search is ended (Step S16; Yes), the correction value created upon production of the plate version 500 (900 in the case of mammography) is used (Step S18).

Next, with reference to FIG. 6, a case where the image input device includes the unevenness correction data structure shown in FIG. 2 and a new material plate or the like is produced, and the like, will be described. In FIG. 2, the plate version range "300–499" is a reserve region to be used when a new material plate or the like is produced.

First, when the plate version range of the inserted cassette is "000–299" (Step S21; "000–299") and there is a correction value of the same plate version (Step S22; Yes), the correction value is used (Step S23). Even when the plate version is different (Step S22; No), an adjacent correction value on the lower or higher side is searched for (Step S24), and, when the correction value is within the range of plate version "000–299" (Step S25; Yes) and there is a correction value of the same plate version (Step S26; Yes), the correction value is used (Step S27). When there is no correction value of the same plate version (Step S26; No), search is performed until the correction value is found. In contrast, when the correction value is not within the range of plate version "000–299" (Step S25; No), the correction value search is ended, and the correction value at the time of production is used (Step S28).

Next, when a new material plate is inserted, or when the plate version range is not within "000–299", the reserve region is used for correction value search (Step S21; "300–499"). When there is a correction value of the same plate version (Step S29; Yes), the correction value is used (Step S30). Even when the plate version is different (Step S29; No), an adjacent correction value on the lower or higher side is searched for (Step S31), and, when the correction value is within the range of plate version "300–499" (Step S32; Yes) and there is a correction value of the same plate version (Step S33; Yes), the correction value is used (Step S34). When there is no correction value of the same plate version (Step S33; No), search is performed until the correction value is found. In contrast, when the correction value is not within the range of plate version "300–499" (Step S32; No), the correction value search is ended, and the correction value at the time of production is used (Step S35).

Figure 6:
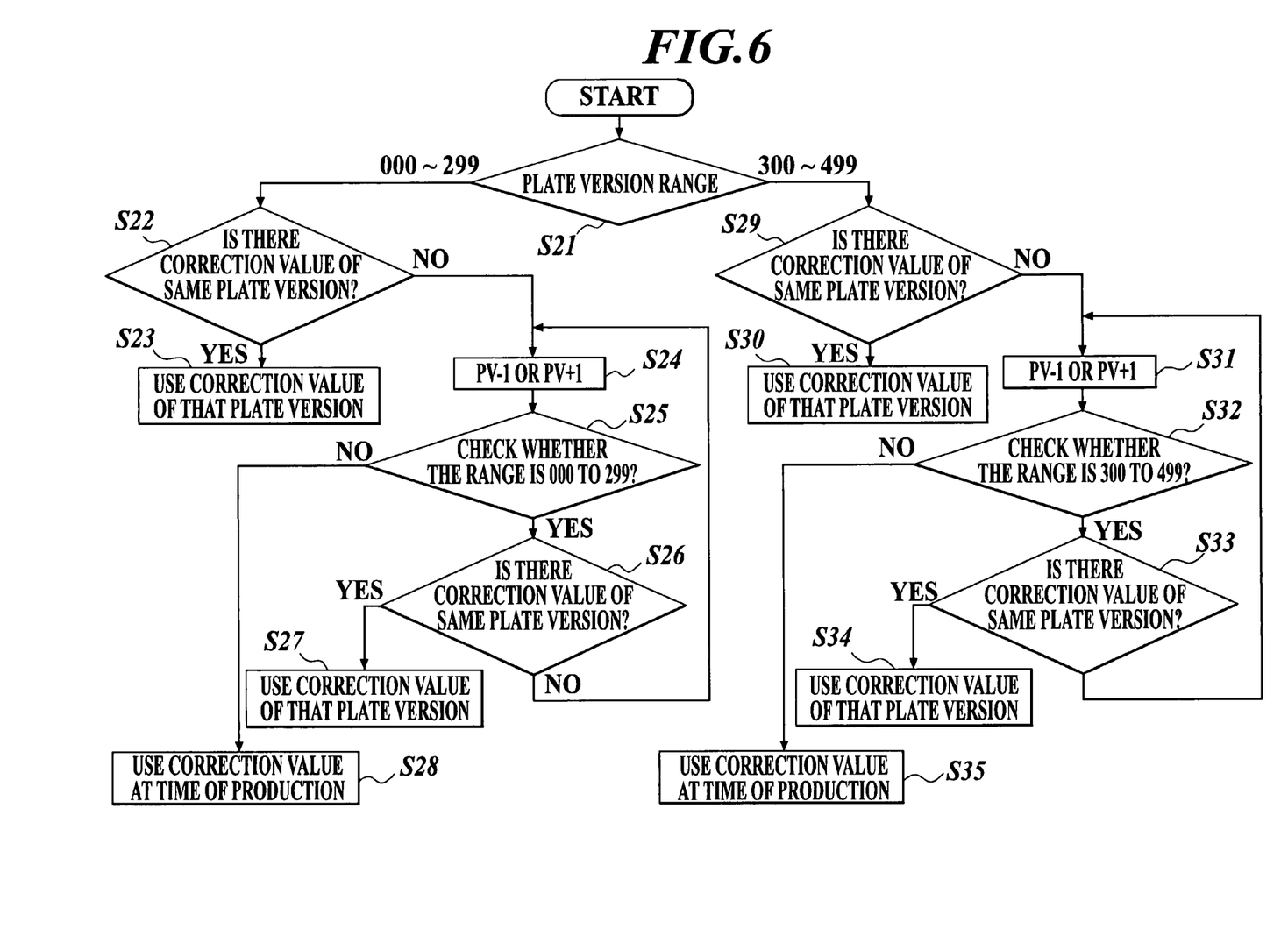
FIG. 6 is a flow chart showing another example of the unevenness amendment selection procedure.

More specifically, for example, upon reading an image on the plate of version "129", a relevant correction value does not exist within the range "000–299" but exists only in the plate version, for example, "341" within "300–499", the correction value "500" at the time of production is used in this embodiment, instead of the correction value of the plate version "341", as shown in FIG. 6 (see Step S25).

Thus, by providing a plate version reserve region beforehand in order for correction for new material plates and plates that requires special correction, it is possible to perform correction for new material plates and special correction easily.

According to this embodiment, to date, with an image input apparatus of CR type that uses cassettes, for example, in a case where there are a plurality of cassette sizes (detection region) such as 14×17 inch size/14×11 inch size/14×14 inch size/10×12 inch size/8×10 inch size/mammography size, etc., the cassette size being one of the correction coefficients, correction value creation (calibration) had to be performed always with the 14×17 inch size that is the largest size, even when, for example, only 10×12 inch size is applied at the user's end who uses a detection device (plate).

However, in the embodiment of the present invention, since a correction value is created for each size, correction value creation only for a 10×12 inch-sized cassette to be used is required. Thus, it is not necessary to specially prepare a cassette of 14×17 inch size, and optimal correction value creation can be performed. Needless to say, the present invention is not limited to the mode of use described herein, and is similarly applicable to a dedicated device of CR type, FPD type and the like.

Moreover, in the image input apparatus, for example, when a correction value is created for a 10×12 inch-sized cassette (detection region), an image may be formed for a smaller-sized cassette (here, 8×10 inch size) by using the correction value created for the 10×12 inch-sized cassette.

Further, in the image input apparatus, in a case where a cassette whose size is larger than 10×12 inch size is selected upon image formation (image reading), for example, when 14×17 inch size is selected, it is preferable not to use the correction value created for 10×12 inch size. At this time, when a correction value is created for 14×17 inch size in addition to the above for, e.g., different plate luminance, correction may be performed while allowing a selecting section to be included to use the above correction value.

Furthermore, in the image input apparatus, even when a correction value is created for a small size, in a case where the correction data (correction value) is not dependent on the cassette size such as a sensitivity correction value, the correction value may be created for any size, and it is possible to use the correction value upon image formation (image reading) for the sizes ranging from 14×17 inch size to 8×10 inch size, without problems.

In the image input apparatus, concerning correction values, for example, when a section to store a correction value used when there is no optimal value as well as a correction value usable unconditionally, and the correction values are created beforehand (for example, at the time of production), correction may be performed at the user's end for, e.g., 10×12 inch size, and an image may be formed by using the correction value usable unconditionally, to read an image of 14×17 inch size.

As for the correction value usable unconditionally, it is preferable that the correction value definitely covers whole range of data, such as correction data of as large a region as possible by preparing a reading size exclusive for correction, which permits correction for a size larger than the standard of the input image apparatus, and, concerning sensitivity, data where a correction value is created using a plate that outputs average sensitivity. When the whole range cannot be covered, it is preferable that the correction data is created for each (for example, when plate types are different and it is impossible to have the same sensitivity correction value due to largely differed luminance, etc.), and that the unconditionally-used correction value is protected against deletion. For example, the correction value usable unconditionally may be created upon correction at the time of shipment of the product, and then overwrite protection or deletion protection may be set thereto, thus allowing correction for various cassette sizes or plates as desired, when correction value creation is performed at the user's end.

Moreover, when a CR type is used as in the case of the present embodiment, for example, version numbers (version data) are assigned to each of plate lots, improved varieties, etc., there are tables showing which of, for example, the cassette size, sampling pitch and plate type (regular plate, high sensitivity plate, mammography plate, etc.) is used for correction value formation in each version, and the tables are memorized together with the correction values.

At the time of image reading, a correction value is selected by obtaining the version number for the read image through, for example, not to mention manual input, barcode input from the barcode on the plate or the cassette, remote input using an IC chip, transmission of the version number of the plate through network, and the like. In this case, as described above, for example, to read an image of 14×14 inch size, from correction value data information for an inputted plate number, the correction value data for the relevant plate number is extracted. However, concerning the correction value data, when correction is performed only for, e.g. 10×12 inch size, the correction value is not usable for reading of 14×14 inch size. In this case, a plate number with a correction value for a size not smaller than 14×14 inch size is searched for in the adjacent plate numbers. Further, in this case, search may be performed from data that has been once obsolete.

Although search is performed based on a size in the above-described embodiment, search may be performed based on, for example, difference in sampling pitches, plate types, reading speeds, X-ray tubes to be used, and the like. Needless to say, even when all conditions are not included, it is possible to combine a function to give highest priority to size. Concerning X-ray tube information and the like, it is possible to receive through network information as to which tube is used for radiography, and the like.

Further, although search is performed for a relevant correction value of an adjacent plate number, when the relevant correction value cannot be found, it is possible to use the above-mentioned correction data usable unconditionally. The feature of the correction data usable unconditionally is the same as that described above.

Furthermore, when there is no relevant correction value, it is also possible to output (input) an image to the controller 18 or the like without correction. In this case, attention may be called to the user through an alarm sound or alarming display to show that the output includes no correction.

Moreover, although there are a plurality of correction values, for example, here the correction values are given to every plate version number, in a case where e.g. ten correction values can be stored in total, it is possible to first overwrite the most obsolete correction value, when the correction values have occupied the storage. No overwrite function is performed to the unconditionally-used correction value, thus preventing this correction value from being overwritten.

Hereinabove, the embodiment of the present invention has been described. The present invention, however, is not limited to the above embodiment, and it goes without saying that various modifications can be made therefor without departing from the gist of the invention.

INDUSTRIAL APPLICABILITY

According to the present invention, by creating a plurality of correction coefficients and correction values, it is possible to perform correction as desired using a detection region (cassette) used on site. Moreover, even when the types of recording members (plate) are different, appropriate correction can be performed, since a plurality of correction values are stored and there is a function to perform selection.

The invention claimed is:

1. A radiographic image input apparatus comprising:
   a detection section which detects radiographic image information from a recording member having the radiographic image information recorded thereon;
   an extraction section which extracts a size of the recording member;
   a storage section which stores a plurality of correction values for correction of at least one of unevenness of the detected radiographic image information and radiography sensitivity of the detection section, said storage section storing respective correction values for a plurality of sizes of recording member;
   a selecting section which selects from the storage section a correction value corresponding to the extracted size of the recording member; and
   a correction unit which corrects at least one of the unevenness of the detected radiographic image information and the radiography sensitivity of the detection section using the selected correction value.

2. The radiographic image input apparatus of claim 1, further comprising a creation section which creates the plurality of correction values corresponding to the sizes of the recording member.

3. The radiographic image input apparatus of claim 1, wherein the selecting section selects the correction value for correcting the unevenness of the detected radiographic image information to correspond to the extracted size not larger than a predetermined size.

4. The radiographic image input apparatus of claim 1, wherein the storage section stores a correction value corresponding to a largest size of recording member that is detectable by the detection section, and the selecting section selects the correction value corresponding to the largest size when the extracted size is not smaller than a predetermined size.

5. The radiographic image input apparatus of claim 1, wherein the storage section stores a correction value corresponding to a largest size of recording member that is detectable by the detection section, and the selecting section selects the correction value corresponding to the largest size when no correction value corresponding to the extracted size is stored in the storage section.

6. The radiographic image input apparatus of claim 1, wherein the selecting section selects a correction value corresponding to a smaller size than the extracted size of the recording member, and the correction unit applies correction values corresponding to the left, right, upper and lower boundaries of the smaller size to left, right, upper and lower regions in the extracted size outside of the left, right, upper and lower boundaries of the smaller size, respectively, to correct the unevenness of the detected radiographic image information.

7. The radiographic image input apparatus of claim 1, wherein the storage section records image information and stores a plurality of version data containing information about the recording member from which the radiographic image information is detected by the detection section, the correction values stored by the storage section correspond to respective versions of recording members, and the selecting section selects the correction value based on relevant version data.

8. The radiographic image input apparatus of claim 1, wherein the selecting section selects the correction value corresponding to a larger size than the extracted size when no correction value corresponding to the extracted size is stored in the storage section.

* * * * *